United States Patent [19]

Bedoit, Jr.

[11] 4,239,907

[45] Dec. 16, 1980

[54] PREPARATION OF LOW VISCOSITY POLYETHER POLYOLS

[76] Inventor: William C. Bedoit, Jr., 2305 Stannye Dr., Louisville, Ky. 40222

[21] Appl. No.: 3,236

[22] Filed: Jan. 15, 1979

[51] Int. Cl.$^3$ .................. C07C 41/00; C07H 15/04
[52] U.S. Cl. .......................... 536/120; 536/1; 568/616; 568/673; 568/675; 568/672
[58] Field of Search ............... 536/120; 568/616, 673, 568/675, 672

[56] References Cited

U.S. PATENT DOCUMENTS

| | | | |
|---|---|---|---|
| 2,733,238 | 1/1956 | Kerr et al. | 536/111 |
| 2,902,478 | 9/1959 | Anderson | 536/120 |
| 3,033,853 | 5/1962 | Klug | 536/111 |
| 3,153,002 | 10/1964 | Wismer et al. | 536/120 |
| 3,169,934 | 2/1965 | Dennett et al. | 536/120 |
| 3,265,641 | 8/1966 | Wismer et al. | 536/1 |
| 3,277,076 | 10/1966 | Yotsuzuka | 536/120 |
| 3,297,597 | 1/1967 | Edwards et al. | 536/1 |
| 3,346,557 | 10/1967 | Patton, Jr. et al. | 536/120 |
| 3,369,014 | 2/1968 | Booth | 536/1 |
| 3,428,683 | 2/1969 | Swenson et al. | 536/1 |
| 3,442,888 | 5/1969 | Deggmger et al. | 536/120 |
| 3,865,806 | 2/1975 | Knodel | 536/120 |
| 3,941,769 | 3/1976 | Maassen et al. | 536/120 |

*Primary Examiner*—Johnnie R. Brown
*Attorney, Agent, or Firm*—Pravel, Gambrell, Hewitt, Kirk, Kimball & Dodge

[57] ABSTRACT

This invention is concerned with the employment of a water-soluble initiator, of sucrose, sorbitiol, trimethylpropane, ammonia or amine and water to form an initiator which is mixed and reacted with alkylene oxide in the presence of water and without the use of an added catalyst to produce polyether polyols for use in the production of urethane foams.

19 Claims, No Drawings

PREPARATION OF LOW VISCOSITY POLYETHER POLYOLS

TECHNICAL FIELD OF THE INVENTION

The present invention relates to the production of low viscosity polyether polyols for preparation of rigid urethane foams. More particularly, the invention concerns the employment of a water-soluble initiator of sucrose or sorbitol or trimethylolpropane, ammonia or alkanolamine or primary alkyl amine or alkylene diamine, and water to form an initiator which is mixed and reacted with ethylene oxide and an alkylene oxide without the use of an added catalyst to produce a polyether polyol to be used in the production of urethane foams.

Prior Art

Various methods have been employed in the past to prepare polyether polyols from sugars. The prior art, however, has been vexed by two major problems: (1) an active catalyst, which requires neutralization and removal at the end of reaction has been essential, and (2) only very small amounts of water could be tolerated in the reaction mixture.

The prior art found it necessary to employ strong acid catalysts or strong base catalysts, such as sodium hydroxide or potassium hydroxide, to effect the addition of alkylene oxides to hydroxyl-containing initiators. See for example, U.S. Pat. Nos. 3,153,002; 3,265,641 and 3,442,888. But such strong catalysts must be neutralized at the end of the alkoxylation reaction and filtered out or removed by ion exchange resins. Both neutralization and removal add costs to the product and often complete removal and neutralization of the catalyst was impossible, leaving unwanted impurities in the product.

Besides sodium or potassium hydroxide, trimethylamine is typical of the catalysts employed in the prior art. See U.S. Pat. No. 3,865,806. Not only is trimethylamine difficult to remove completely, but an undesirable fishy odor is left behind in the polyol after removal of the catalyst. Additionally, trimethylamine has a much slower and, thus, commercially unfavorable reaction rate.

Another problem of the prior art is its intolerance to the presence of water. For example, U.S. Pat. Nos. 3,297,597; 3,442,888 and 3,865,806 emphasize that the amount of water must not exceed 0.5 or 1%. The necessity of lowering water content to such tolerance levels can be quite an operating disadvantage, particularly when a normally solid initiator, such as sucrose, is used. Sucrose, or sugar, is a highly desirable initiator to use for a polyether polyol for rigid foams because of its low cost and high functionality.

Finally, the production of polyurethane foams suffers from the high viscosities that are prevalent in amino polyether polyols derived from sugars. Viscosities, such as 15,000 cp. Brookfield are quite common. This results in the expenditure of additional energy for reactant transport and handling.

In addition, sucrose-derived polyols in the past have produced inferior urethane foams when polymerized with organic polyisocyanates and isocyanurates because of their poor compatibility with such reactants. The present invention removes such difficulties by the use of nitrogen from ammonia, alkanolamines, primary alkyl amine or alkylene diamine. The presence of nitrogen in the polyether polyol aids its reactivity and compatability with organic polyisocyanates and isocyanurates.

SUMMARY OF THE INVENTION

The practice of the process of the present invention produces a low viscosity, amino polyether polyol which can be polymerized with organic polyisocyanates and isocyanurates to yield polyurethane and polyisocyanurate foams of highly desirable characteristics. The amino polyol is prepared by the process of this invention from a water-soluble initiator composition, preferably sucrose or sorbitol, ammonia or an alkanolamine or a primary alkyl amine having one to four carbon atoms or alkylene diamine, and water. Water is not only tolerated but is employed as a desirable ingredient in the reaction. The initiator composition is mixed and reacted in an alkoxylation reaction, preferably in block sequence, with ethylene oxide and an alkylene oxide having from three to four carbon atoms. There is no need for an added alkoxylation catalyst, nor for its subsequent removal. An in situ catalyst is believed to result from the reaction of the ammonia, alkanolamine, primary alkyl amine or alkylene diamine and the alkylene oxide. The reaction is conducted at elevated temperatures, not greater than 110° C., and pressures for a time sufficient to produce a polyether product having the desired hydroxyl number.

In the practice of the inventive process, it must be emphasized that reaction time and viscosity are significantly reduced from the prior art practices. Further, by changing the amount and order of addition of ethylene and alkylene oxide, reactivity, molecular weight and foam characteristics, such as set time, rise time and humid aging properties can be varied over a wide range.

DETAILED DESCRIPTION

The reactor, usually a pressure vessel such as an autoclave, is charged with a water-soluble initiator of sucrose, sorbitol or trimethylolpropane, or mixtures thereof, along with water and ammonia or alkanolamine or primary alkyl amine or alkylene diamine. The water-soluble initiator is usually charged in the form of an aqueous solution. The proportions of these reactants can be varied according to the functionality and viscosity desired. Although initiators having a functionality as high as 6 and 8, in the instance of sucrose, are often employed to make polyether polyols, the average functionality desired in the finished polyol is generally from about 4.0 to about 4.6. Where the chain length of the finished polyol is short enough, the average functionality may be as low as 3.

It is very desirable to use the lowest polyol functionality that will give the desired foam properties. This is because the viscosity of the polyol will be minimized and, thus, storage and handling simplified. A key advantage of the present invention is that polyether polyols can be produced with low viscosities, such as 5000–7000 cp. Brookfield, and those same polyols will still produce desirable rigid polyurethane foams. Sucrose has a functionality of 8, whereas ammonia has a functionality of 3 and water when reacted with an alkylene oxide has a functionality of 2. By altering the proportions of the reactants, the functionality of the polyol can be varied. Since I discovered, contrary to popular belief, that most of the water does not enter the reaction in the practice of this invention, the presence of water, surprisingly, does not lower the functionality a great deal. Thus, in determining the desired proportions of initiators, the unreacted water must be taken into account.

In the practice of the process of this invention an aqueous solution of the water-soluble initiator containing as much as 50% water by weight can be tolerated. At least enough water is required in the practice to hold the initiator in suspension, but of course a homogeneous solution is desirable. While any amount of water up to about 50% may be used, the preferred amount of water to be included in the reaction mixture is from about 14% by weight to about 20% by weight. Conversely, the aqueous solution of the water-soluble initiator could be said to contain from about 80% by weight to about 86% by weight of the initiator, particularly in the case of sucrose.

About 0.3 moles to about 0.7 moles of water per equivalent of water-soluble initiator can be used and preferably, about 0.4 moles of water in order for the weight percent of water to be about 3.5% of the total. More or less water can be employed as stated above. It is important to note here that some teachings of the prior art demanded that the water content be less than 0.2%.

From about 0.4 to about 0.6 equivalents of ammonia, alkanolamine, primary alkyl amine or alkylene diamine per equivalent of water-soluble initiator can be employed, with about 0.5 equivalents of ammonia, alkanolamine, primary alkyl amine or alkylene diamine per equivalent being the preferred proportion. Examples of the diamines that can be employed are ethylenediamine, propane diamine, propylenediamine, hexamethylenediamine and other alkylene diamines and primary alkyl amines. The term primary alkyl amine as used herein includes primary monoamines having from two to four carbon atoms and diprimary amines having from three to about six carbon atoms. An alkanolamine is defined as a compound with two to four carbon atoms in the hydroxyl alkyl groups. Diethanolamine is a simple alkanolamine which works quite well. By altering the proportion of ammonia, alkanolamine, alkyl amine or alkylene diamine in the initiator mixture, the reactivity of the polyether polyol with polyisocyanates and isocyanurates can be varied since tertiary amines are known to exhibit catalytic activity for the urethane reaction. One advantage of the process of this invention is the ability to vary that activity.

The ammonia, alkanolamine, primary alkyl amine or alkylene diamine not only reacts with the alkylene oxide to provide an internal catalyst, but it also permits an increased percentage of the initiator, especially sugar, to go into solution before saturation occurs. For instance, with the present invention, an initiator solution can be employed containing, by weight, 8.60 parts sugar, 1.43 parts of water and 0.574 parts ammonia. This represents a sugar concentration of 85.75% by weight in aqueous solution, which would be super-saturated at 90° C. without the presence of ammonia. In a sugar concentrated solution such as this, it is desirable to finish the alkoxylation step completely before removing the unreacted water. In this embodiment, approximately one-third of the water serves as an initiator, and enters into reaction with the alkylene oxide and two-thirds is removed, usually by vacuum distillation. In other instances in the practice of this invention, some of the water is removed after sufficient alkylene oxide has been added to render the ammonia, alkanolamine, alkyl or alkylene diamine essentially non-volatile. This is done where it is generally desirable to start with higher concentrations of water in the initiator, such as 20 wt. percent or more.

Ethylene oxide and an alkylene oxide having 3 to 4 carbon atoms are mixed and reacted with the initiator composition at elevated temperatures not exceeding 110° C., usually about 60° to 110° C., and preferably from about 80° to about 95° C. Alkylene oxides which have been successfully employed include propylene oxide, butylene oxide, tetrachlorobutylene oxide and epichlorohydrin. Other halogenated alkylene oxides may be used for the preparation of fire retardant polyols. Alkoxylation pressures range from 1.0 to about 6.6 kg/cm$^2$, with 1.0 to about 4.2 kg/cm$^2$ preferred. An additional advantage of this invention is that the alkoxylation pressure can be held below about 2.8 kg/cm$^2$ once the reaction passes the initiation point.

For the preparation of conventional rigid urethane foams, the total quantity of ethylene oxide employed in preparing the polyether polyol preferably should not exceed 15% of the total alkylene oxide used. With higher ethylene oxide levels, the humid aging properties of the foam made from such a polyol deteriorate somewhat. However, this undesirable characteristic will not be apparent in high-density rigid urethane foam applications. In order to obtain a commercially feasible reaction rate, the amount of ethylene oxide utilized should be between 0.25% and 15% by weight of the total alkylene oxide used, and more desirably, 7% to 14%. The use of lower levels of ethylene oxide requires an external catalyst of the type already described in order to form the polyether polyol.

The block addition sequence of Example 1 hereinafter described, which involves adding 0.5 equivalents of ethylene oxide (equiv. wt. 44) followed by 2.2 equivalents of propylene oxide (equiv. wt. 58) per equivalent of the water-soluble initiator, produces a polyol which is highly reactive with polymeric isocyanate, that is, an isocyanate made from the reaction of aniline and formaldehyde. But if the block addition sequence is varied as in the recipe described in Example 4 where 0.07 equivalents of propylene oxide are added before the 0.10 equivalents of ethylene oxide followed by 0.39 equivalents of propylene oxide, the polyol derived therefrom is much less catalytically active with isocyanates. This is evident from an examination of Table III, Examples 11 and 12. The tack free and rise times of Example 12, derived from the polyol of Example 4, increased almost 50% from the times of Example 11 and the Example 1 polyol.

The alkoxylation time of the second block addition sequence also increases. By-product formation and product color are improved. Additionally, the ethylene oxide and alkylene oxide can be mixed together and added to the initiator in a single reaction, as in Example 7. Thus, it is seen that the process of this invention is quite versatile.

A combination of ethylene oxide and alkylene oxide and sequence of reaction with the initiator, can be chosen to give the most favorable reaction time consistent with the desired product quality. For example, greater amounts of ethylene oxide will increase the reactivity of the polyol with polyisocyanates but will also decrease the hydrolytic stability of the resulting urethane foam. In addition, the polyols produced by the present invention can be mixed with commercially available polyols to produce urethane foams.

In conclusion, not only can the reactivity of the finished polyol with isocyanates and isocyanurates be varied by the order of addition of ethylene oxide and alkylene oxide, but the molecular weight, product color and by-product formation in the making of the polyol can be controlled by the manner and order of addition of ethylene oxide and alkylene oxide. By controlling the reaction conditions involved in the preparation of the polyether polyols, products with hydroxyl numbers ranging from 200 to 800 may be obtained.

The following examples are used to illustrate the process of this invention. Of course, it should be understood that reactants, proportions of reactants, and time, temperature and pressure of the reaction may be varied in accordance with the foregoing discussion with much the same results achieved. Thus, the examples should be construed as illustrative and not limiting.

EXAMPLES 1-3

Table I shows the data of polyether polyol preparation following the process of this invention. In the following examples, a ten gallon, jacketed pressure reactor equipped with a stirrer, outside cooling loop, pressure and temperature gauges, stripping column, vacuum pump and nitrogen purge was employed. Tanks mounted on scales were used to accurately measure the ethylene and alkylene oxide addition rate. The procedure employed was to purge the reactor with nitrogen and charge the polyhydric initiator. The desired amount of ammonia or amine or diamine, and water were then added and mixed with the initiator to form a solution. The resulting mixture constituted the initiator composition to which the ethylene and alkylene oxides were added over a period of time in sequence by switching from one feed tank to another.

The reaction was continued, with temperature being controlled in the range indicated, until the total desired amount of oxide had been added and then the mixture was digested for about thirty minutes to insure complete reaction. Usually, no more pressure drop in the vessel was noted after about fifteen minutes of digestion time indicating that no more oxide was being reacted. The reactor contents were then heated to 108° C. and vented. No attempt was made to recover unreacted alkylene oxide since the amount was usually quite small. The water and by-product organic materials were removed by heating the contents of the reactor, with stirring, to 146° C. at 30 mm. Hg. pressure. Example 10 was heated to 150° C. at 10 mm. Hg. pressure. The vacuum was relieved by the addition of nitrogen. The reactor contents were then pumped from the reactor through 100-mesh screen into a five gallon can previously purged with nitrogen.

Examples 1-3 produced satisfactory, if not superior, polyether polyols of low viscosity as shown from the product analyses of Table II. These polyols were prepared by a simple two-step addition of ethylene oxide followed by alkylene oxide. In Example 2, the amount of alkylene oxide, propylene oxide in this case, was increased some thirty percent. The resulting viscosity was much lower, 3920 cp. Brookfield at 24.5° C. In Example 3, the water content was increased to 0.6 moles of water per equivalent of sugar from the 0.4 moles of water per equivalent of sugar utilized in Example 1. The starting sugar concentration in the water was eighty percent and some propylene glycol was stripped from the product. This occured at a final kettle temperature of 152° C. at 6 mm. Hg. pressure. After the water had been removed at 146° C. at 30 mm. Hg., 5.06 kilograms of propylene glycol was recovered. The viscosity of Example 3 was a quite satisfactory 8,660 cp. Brookfield at 25.0° C.

EXAMPLES 4-6

In Examples 4-6, the procedure of the first three examples was modified. Propylene oxide was initially mixed and reacted with the aqueous sugar and ammonia initiator in the pressure vessel charged as previously described followed by ethylene oxide, and then a second block of propylene oxide. In Examples 5 and 5a, the initial concentration of sugar was lowered to eighty weight percent by increasing the amount of water from 0.4 moles per equivalent of sugar to 0.6 moles of water per equivalent of sugar. After mixing and reacting the first propylene oxide block by slowly adding same and maintaining the temperatures shown in Table I, ninety percent of the ethylene oxide was added. The reaction was interrupted by stopping the addition of ethylene oxide and some water, about 0.056 and 0.103 moles, respectively, was removed under vacuum. Then, the remaining ten percent of the ethylene oxide block was added followed by the last of the propylene oxide. The time for the stripping of water was excluded from the total oxide addition time. In Example 6, the amount of propylene oxide added in the first oxide addition step was increased from 0.35 equivalents per equivalent of sugar to 0.475 equivalents propylene oxide per equivalent of sugar. The reaction proceeded less actively and a long reaction time resulted for this example. This reaction time can be reduced by adding the alkylene oxide at a higher temperature, such as, 95° to 100° C. The viscosity of the polyol remained quite low, 8480 cp. Brookfield at 25.2° C., as reflected in Table II.

EXAMPLES 7-10

In Example 7, a polyol was prepared by employing a one-step addition of mixed oxides. The 13.14 kg of the oxide blend used consisted of 14.6% ethylene oxide and 85.4% propylene oxide. Except for the long oxide reaction time of six hours and eleven minutes, polyol properties comparable to those of the first six examples were obtained.

Example 8 demonstrates the use of sorbitol instead of sugar as the water-soluble initiator. Following the procedures described above to prepare the polyether polyol, the viscosity of the resulting polyol was quite low, 4100 cp. Brookfield at 21.8° C. and the time period over which the oxide was added, mixed and reacted was only two hours and sixteen minutes. A two-step addition of an ethylene oxide block followed by a propylene oxide block was employed as in Example 1, previously described.

Example 9 is included to show that diethanolamine will serve just as well as ammonia when used as part of the initiator. A two-step addition of ethylene oxide and propylene oxide was employed as in Example 1, previously described. It is to be expected that other commercial alkanolamines will produce polyether polyols with similar properties.

Example 10 was performed to demonstrate the use of an alkylene diamine, ethylene diamine specifically, in place of ammonia. Other than this change, the process steps were the same as for Example 5 above. Although Table I indicates that viscosity is somewhat high and the reaction time is over five hours, the sucrose based polyether polyols of this example were found to yield equivalent foam properties when tested in foam formulation. Note on Table II this polyether polyol had a higher functionality. The foam properties which result of this use of ethylene diamine are shown in Table II, Example 13.

134, sold under the trademark "PAPI" by UpJohn as the polymeric isocyanate. The physical properties of the resulting rigid, urethane foams are shown in Table III. The below formulation was used throughout.

TABLE I
POLYOLS FROM SUGAR AND SORBITOL

| | Initiator Charged | | | Alkylene Oxide Block Polymers | | | |
|---|---|---|---|---|---|---|---|
| | Equivalents | | Lb. Moles | Propylene Oxide (eq) | Ethylene Oxide (eq) | Propylene Oxide (eq) | Total Oxide |
| Example | Sugar | NH₃ | H₂O | Temp. °C. | Temp. °C. | Temp. °C. | Reaction Time |
| 1* | 0.201 | 0.101 | 0.079 | | 0.102 60–78 | 0.457 72–95 | 3 hours 28 minutes |
| 2 | 0.201 | 0.101 | 0.079 | | 0.102 66–72 | 0.569 62–99 | 3 hours 30 minutes |
| 3 | 0.201 | 0.101 | 0.119 | | 0.100 82–86 | 0.476 76–95 | 2 hours 47 minutes |
| 4 | 0.201 | 0.101 | 0.079 | 0.071 87–94 | 0.103 87–100 | 0.386 88–96 | 3 hours 25 minutes |
| 5 | 0.201 | 0.101 | 0.119 | 0.069 87–92 | 0.100 90–92 | 0.379 88–92 | 3 hours 37 minutes |
| 5a | 0.201 | 0.101 | 0.120 | 0.069 87–91 | 0.100 89–93 | 0.379 91–105 | 3 hours 50 minutes |
| 6 | 0.201 | 0.101 | 0.120 | 0.095 | 0.1026 | 0.362 | 5 hours 15 minutes |
| 7 | 0.201 | 0.101 | 0.079 | Oxide Blend (14.6% EO, 85.4% PO) | | | 6 hours 11 minutes |
| 8 | 0.200 Sorbitol | 0.101 | 0.079 | | 0.102 80–96 | 0.459 7–103 | 2 hours 16 minutes |
| 9 | 0.201 | 0.101 Diethanol Amine | 0.079 | | 0.034 78–90 | 0.457 88–110 | 2 hours 10 minutes |
| 10 | 0.201 | 0.100 Ethylene Diamine | 0.120 | 0.069 | 0.100 | 0.379 | 5 hours 39 minutes |

*Sugar charged 8.60 pounds (3.90 kg)
NH₃ charged 0.57 pounds (0.25 kg)
H₂O charged 1.43 pounds (0.65 kg)
EO charged 4.50 pounds (2.04 kg)
PO charged 26.50 pounds (12.02 kg)

TABLE II
POLYOLS FROM SUGAR AND SORBITOL
Product Analyses

| Example | Wt. kgs. | OH No. | Mol. Wt. | Functionality | Amine meq./g. | Viscosity cp. |
|---|---|---|---|---|---|---|
| 1 | 17.46 | 485 | 527 | 4.5 | 0.83 | Kinematic 7068 @ 25° C. |
| 2 | 20.18 | 425 | 488 | 3.8 | 0.71 | Brookfield 3920 @ 24.5° C. |
| 3 | 17.34 | 470 | 445 | 3.7 | 0.78 | Brookfield 8660 @ 25.0° C. |
| 4 | 17.80 | 489 | 505 | 4.4 | 0.80 | Brookfield 7820 @ 23.8° C. |
| 5 | 17.52 | 509 | 497 | 4.5 | 0.86 | Brookfield 7600 @ 25.8° C. |
| 5a | 16.48 | 520 | 574 | 5.3 | 0.96 | Brookfield 17500 @ 25.0° C. |
| 6 | 17.14 | 486 | 507 | 4.4 | 0.88 | Brookfield 8480 @ 25.2° C. |
| 7 | 16.29 | 545 | 482 | 4.7 | 0.74 | Brookfield 6800 @ 28.0° C. |
| 8 | 15.80 | 538 | 414 | 4.1 | 0.91 | Brookfield 4100 @ 21.8° C. |
| 9 | 17.35 | 513 | 493 | 4.5 | 0.81 | Kinematic 6698 @ 25.0° C. |
| 10 | 16.81 | 476 | 665 | 5.7 | 0.80 | Brookfield 15160 @ 25.6° C. |

EXAMPLES 11–13

Polyether polyols of Examples 1, 4, and 10 were used to prepare a nominal 32 kilograms per cubic meter rigid polyurethane foam using polymethylene polyphenyl polyisocyanate having an equivalent weight of about

| | Parts by Weight |
|---|---|
| Polyol | 37.5 |
| DC-193 Silicone Surfactant | 0.5 |
| 33% of triethylene diamine in propylene glycol sold under the trademark DABCO 33LV | 0.5 |
| Fluorocarbon 11 B | 14.7 |
| Polymeric isocyanate | 46.8 |

This formulation gives a foam density of about 30.4 to 31.3 kilograms per cubic meter. Higher densities were obtained by decreasing the amount of fluorocarbon blowing agent. The isocyanate index was held at 105. In Example 12, an additional 0.5 parts by weight of dimethylethanol amine were added to the above formulation. All foams were poured through a 2-component, low-pressure foam machine at a temperature of 25° C. into a 16.5 cm by 16.5 cm by 20.3 cm box. After three days of aging, the foams were cut into rectangular shaped blocks of 10.16 cm by 12.7 cm by 2.54 cm and tested according to standard ASTM procedures. The results are listed in Table III.

The foam preparations of Examples 11 through 13 also demonstrate the variance in reactivity obtainable. The formulation of Examples 11 and 12 were identical. The polyol preparation was varied. A comparison of the tack free time and rise time show that the catalytic contribution of the polyol was greater in Example 11 than Example 12. Example 12 was rerun with 0.5 parts by weight of a dimethylethanolamine added. This run gave a tack free time of 103–105 seconds and a rise time of 135–139 seconds. Thus, it is demonstrated that the variance in the process within the scope of this invention allows a variance of catalytic activity of the polyol. In this instance it is equivalent to the amount of catalyst added in the example to reduce the times measured.

The foams prepared in Examples 11 through 13, reported in Table III were provided to demonstrate that the low viscosity polyether polyols prepared by the practice of this invention produce satisfactory, if not superior, rigid polyurethane foams. It will be recognized by those skilled in the art that all of the polyols prepared in Examples 1 through 10 will produce satisfactory urethane foam because their OH number, functionality, and viscosity are favorable. These polyether polyols may also be combined with isocyanurates to produce an acceptable foam. Polyols having OH numbers and functionalities similar to those of Examples 1 through 10 are in successful commercial use today, but many of these polyols fail to exhibit foam properties as desirable as those shown in Examples 11 through 13 and certainly the method of their manufacture does not have the advantages of those in the practice of this invention.

To compare reactivity of the polyols prepared in accordance with this invention, foams were prepared using equivalent formulations and the cream time, tack free time and rise time compared. The times were almost the same even though the commercially available sucrose polyol (Poly G-Olin Chemical Corporation) had an amine content of 1.45 meq./gm. as compared with the lower amine content of the polyol of this invention.

Because of the foregoing, many varying and different embodiments may be made by those skilled in the art without departing from the scope of the inventive concept herein taught or the claims appended hereto.

TABLE III

FOAM PROPERTIES

| Example | Cream Time Seconds | Tack Free Time Seconds | Rise Time Seconds | Density kg/m$^3$ | Compression Yield Strength kg/cm$^2$ | Cold Aging 1 Week at −27° C., % ΔV/ΔL/ΔW | Dry Heat Aging 1 Week at 82° C., % ΔV/ΔL/ΔW | Humid Aging 1 Week at 70° C. 100% R.H., % ΔV/ΔL/ΔW | Polyol From Example No. |
|---|---|---|---|---|---|---|---|---|---|
| 11 | 39 | 109 | 146 | 31.34 | 2.67 | +0.17/+0.28 /−0.19 | +2.81/+1.59 /+0.45 | +8.02/+4.04 /−0.81 | 1 |
| 12 | 38 | 152 | 206 | 29.30 | 2.25 | +0.38/+0.26 /−0.10 | +2.49/+1.82 /+0.42 | +8.33/+3.75 /−2.67 | 4 |
| 13 | 29 | 78 | 107 | 32.05 | 3.06 | +0.85/+0.65 /0.00 | +3.49/+1.84 /+2.71 | +8.99/+6.12 /−0.18 | 10 |

I claim:

1. In a process for preparing a polyether polyol which comprises reacting a polyhydric water-soluble initiator with ethylene oxide and an alkylene oxide in the presence of ammonia or an alkanolamine or a primary alkylamine or alkylene diamine, the improvement which comprises:

mixing and reacting the water-soluble polyhydric initiator and ammonia or alkanolamine, having two to four carbon atoms, or primary mono alkylamine having two to four carbon atoms, or diprimary amine having three to about six carbon atoms, or alkylene diamine having from two to six carbon atoms, in the presence of added water with ethylene oxide and the alkylene oxide at an elevated temperature not greater than about 110° C. in the absence of an added alkoxylation catalyst.

2. The process of claim 1 where the water-soluble initiator is sucrose.

3. The process of claim 1 where the water-soluble initiator is sorbitol.

4. The process of claim 1 where the alkanolamine is diethanolamine.

5. The process of claim 1 where the alkylene diamine is ethylene diamine.

6. The process of claim 1 where the alkyl diamine is 1,3-propanediamine.

7. The process of claim 1 where the alkylene oxide is propylene oxide.

8. The process of claim 1 where the alkylene oxide is butylene oxide.

9. The process of claim 1 where the alkylene oxide is a halogenated alkylene oxide.

10. The process of claim 1 where ethylene oxide is mixed and reacted followed by the alkylene oxide in block sequence.

11. The process of claim 1 where the alkylene oxide is mixed and reacted with the initiator followed by ethylene oxide and a final amount of alkylene oxide in a block sequence.

12. The process of claim 1 where the ethylene oxide and an alkylene oxide are mixed and reacted with the initiator in a single addition step.

13. The process of claim 1 where the water-soluble initiator is an aqueous solution containing 80–86% by weight sugar.

14. The process of claim 1 where water is removed from the polyether polyol after reaction of the ethylene oxide and alkylene oxide with the initiator.

15. The process of claim 1 where water is removed from the reactor after sufficient ethylene oxide or alkylene oxide has been reacted with the initiator to render the ammonia, alkanolamine, or primary mono-alkyl amine or diprimary amine or alkylene diamine nonvolatile, but prior to the reaction of all such oxides.

16. In a process for the preparation of a polyether polyol from a water-soluble polyhydric initiator by reacting the initiator with ethylene oxide and an alkylene oxide, the improvement which comprises the steps of:

charging a reactor with, (1) as the water-soluble initiator, sucrose, sorbitol or a mixture thereof; (2) about 0.3 to about 0.7 moles of water per hydroxyl equivalent of the water-soluble initiator; and (3) about 0.4 to about 0.6 equivalents of ammonia, diethanolamine, ethylene diamine, propane diamine, propylene diamine or hexamethylene diamine per hydroxyl equivalent of water-soluble initiator;

mixing and reacting, absent an added alkoxylation catalyst, at a temperature of from about 60° to about 111° C. and a pressure of from about 1.0 to about 6.6 kg/cm$^2$, from about 0.4 to about 0.6 equivalents ethylene oxide per hydroxyl equivalent of the initiator and from about 2.0 to about 3.0 equivalents propylene oxide per hydroxyl equivalent of the water-soluble initiator in a block sequence for a time of from about 2 to about 7 hours, to form a polyether polyol with a molecular weight of 400 to 600 and an OH number of 450 to 550.

17. The process of claim 16 including the steps of:
  interrupting the alkoxylation step;
  removing water from the reaction mixture; and
  continuing the alkoxylation step to form the polyether polyol.

18. The process of claim 16 where the water-soluble initiator is sucrose and is present in the reactor as an about 50 weight % to about 86 weight % aqueous solution.

19. The process of claim 1 wherein ammonia is in the reaction mixture with the water-soluble initiator.

* * * * *